United States Patent [19]

Temple, Jr. et al.

[11] 4,305,944
[45] Dec. 15, 1981

[54] N-[(4-[3-CYANO SUBSTITUTED PYRIDYL]PIPERAZINO)ALKYL]-AZAS-PIRODECANEDIONES

[75] Inventors: Davis L. Temple, Jr., Evansville; Joseph P. Yevich, Newburgh; Walter G. Lobeck, Jr., Evansville, all of Ind.

[73] Assignee: Mead Johnson & Company, Evansville, Ind.

[21] Appl. No.: 184,677

[22] Filed: Sep. 8, 1980

[51] Int. Cl.³ ............... C07D 241/04; A61K 31/445; A61K 31/44; A61K 31/495

[52] U.S. Cl. .................... 424/250; 544/362; 544/230

[58] Field of Search ............... 544/230, 364; 424/250

[56] References Cited

U.S. PATENT DOCUMENTS

| 3,398,151 | 8/1968 | Wu | 260/268 |
| 3,717,634 | 2/1973 | Wu et al. | 260/256.4 N |
| 3,907,801 | 9/1975 | Wu et al. | 260/268 BC |
| 3,976,776 | 8/1976 | Wu et al. | 424/251 |
| 4,182,763 | 1/1980 | Casten et al. | 424/251 |

OTHER PUBLICATIONS

Wu, et al., Journal of Medincinal Chemistry, vol. 12, pp. 876–881 (1969).
Wu, et al. Journal of Medicinal Chemistry, vol. 15, No. 5, pp. 477–479 (1972).

Primary Examiner—Donald G. Daus
Assistant Examiner—Sharon A. Gibson
Attorney, Agent, or Firm—Robert H. Uloth; Robert E. Carnahan

[57] ABSTRACT

2-[4-[4-(7,9-Dioxo-8-azaspiro[4.5]decan-8-yl)butyl]-1-piperazinyl]pyridine-3-carbonitrile, 2-[4-[4-(7,9-dioxo-8-azaspiro-[4.5]decan-8-yl)butyl]-3-methyl-1-piperazinyl]-pyridine-3-carbonitrile and 8-[4-[4-(3-methoxy-2-pyridinyl)-1-piperazinyl]butyl]-8-azaspiro-[4.5]decane-7,9-dione are psychotropic compounds.

7 Claims, No Drawings

N-[(4-[3-CYANO SUBSTITUTED PYRIDYL]PIPERAZINO)ALKYL]-AZASPIRODE-CANEDIONES

FIELD OF THE INVENTION

This invention is concerned with chemical compounds having three heterocyclic components of which the central component is a piperazine ring which is substituted at the 1- and 4- positions by other heterocyclic systems one of which is pyridine (Class 544, Subclass 364).

SUMMARY OF THE INVENTION

The compounds of this invention have Formula I wherein $R^1$ and $R^2$ are selected from hydrogen and methyl, and $R^3$ is cyano or methoxy. The pharmaceutically acceptable acid addition salts are also included.

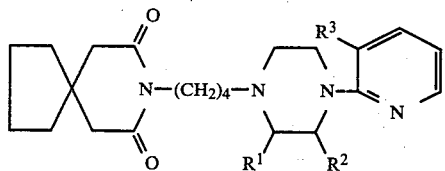

Formula I

These compounds are psychotropic agents which have advantages for the latter purpose due to their lack of extrapyramidal and adrenergic blocking effects in psychotropically effective doses. They are prepared by the application of known synthetic methods to the appropriate starting materials.

DESCRIPTION OF THE PRIOR ART

The structures of four compounds of the prior art, Compound Nos. 1, 2, 3, and 6, and three compounds of the present invention, Compound Nos. 4, 5, and 7 are illustrated in the following table.

Structures $N-(CH_2)_n-N\quad N-B$

| Cmpd. No. | n | B |
|---|---|---|
| 1 | 2 | 2-pyridyl |
| 2 | 3 | 6-methoxy-2-pyridyl |
| 3 | 4 | 2-pyridyl |
| 4 | 4 | 3-cyano-2-pyridyl |
| 5 | 4 | 3-cyano-2-pyridyl* |
| 6 | 4 | 2-pyrimidyl |
| 7 | 4 | 3-methoxy-2-pyridyl |

*3-Methylpiperazine is substituted for piperazine as the central ring; B is located in the piperazine 1-position.

Compound Nos. 1, 2, 3, and 6 are the subjects, with others of the same structural type, of a publication by Wu, et al., entitled "Psychosedative Agents. 2. 8-(4-Substituted 1-Piperazinylalkyl)-8-azaspiro[4.5]decane-7,9-diones", Journal of Medicinal Chemistry, 1972, Vol. 15, No. 5, pages 477-479, in which they are referred to by the same numbers as herein, and of U.S. Pat. No. 3,717,634 patented Feb. 20, 1973, U.S. Pat. No. 3,907,801 patented Sept. 23, 1975, and U.S. Pat. No. 3,976,776, each by Wu, et al., where these substances are described as psychotropic agents having properties typical of the major tranquilizers such as chlorpromazine. The later two patents are divisions of the earlier. The disclosures of U.S. Pat. Nos. 3,717,634, 3,907,801, and 3,976,776 are incorporated herein by reference.

Compound Nos. 3 and 6 in the foregoing table are referred to in the Wu, et al. patents are preferred members of the series. Refer, to Column 3, lines 1-12, of the second Wu, et al. patent. A more remotely related group of compounds is disclosed in an earlier patent and publication of Wu, et al., U.S. Pat. No. 3,398,151 patented Aug. 20, 1968 and Journal of Medicinal Chemistry, Vol. 12, pages 876-881 (1969) which refer to compounds having the general formula shown in the table, but in which the B substituent is phenyl or substituted phenyl.

U.S. Pat. No. 4,182,763 patented Feb. 8, 1980 by Casten, et al. refers to the anxiolytic use of Compound No. 6 where it is referred to by the name buspirone. The disclosure of the Casten, et al. patent is also incorporated herein by reference. U.S. Food and Drug Administration approval for the use of buspirone for the treatment of anxiety neurosis was being sought as of the filing date hereof.

DETAILED DESCRIPTION OF THE INVENTION

Biological test data related to the psychotropic action of Compound Nos. 1-7 and attendant side effects of CNS depression and alpha-adrenergic blocking action are shown in the following table. Values obtained for chlorpromazine are included for reference.

Biological Tests

I. CAR-ED$_{50}$ (mg/kg. of body weight) fasted rat treated orally (psychotropic).
II. CAR-ED$_{50}$ (mg/kg. of body weight) fed rat treated intraperitoneally (psychotropic).
III. AED$_{-0.3}$ (mg/kg. of body weight) activity cage mouse treated orally (CNS depression).
IV. AED$_{-0.3}$ (mg/kg. of body weight) activity cage, mouse treated intraperitoneally (CNS depression).
V. Receptor binding assay, IC$_{50}$ in nM, tritiated siperone as ligand (psychotropic).
VI. Receptor binding assay, IC$_{50}$ in nM, tritiated WB-4101 as ligand (alpha-adrenergic blockade).
VII. IC$_{50}$ (mcg/ml) alpha-adrenergic receptor blocking action in vitro - rat seminal vesicle - l-norepinephrine as spasmogen.

| Cmpd. No. | I | II | III | IV | V | VI | VII |
|---|---|---|---|---|---|---|---|
| 1 | — | 22.6 | — | 41 | — | — | 2.08 |
| 2 | — | >50 | 82 | 7.4 | — | 48 | 0.073 |
| 3 | 34 | 2.8 | 10 | 2.6 | 960 | 280 | 0.335 |
| 4 | 24 | — | 97 | — | 110 | 360 | — |
| 5 | 85 | — | — | — | 400 | — | — |
| 6 | 48 | 4.3 | 92 | 33 | 120 | 1400 | 3.5 |
| 7 | 55 | — | — | — | 100* | 65 | — |
| Chlorpromazine | 39 | 4.8 | — | 3.6 | 40 | 31 | 0.0132 |

*Average of two determinations.

Tests I and II refer to the conditioned avoidance response. Data with respect to Test II were obtained by the method described in the above Wu, et al. patents and publications in which trained rats were maintained on a standard laboratory diet and were treated intraperitoneally with the test drug. Test I is a modification of the same conditioned avoidance response test except that fasted rats were employed and the animals were treated orally. Comparison of the data from Tests I and II for Compound Nos. 3, 6, and chlorpromazine suggests that the values obtained treating fasted rats orally are approximately 8 to 12 times (indicating less activity) those obtained employing the intraperitoneal route of administration with fed rats.

Test IV involves measurement of spontaneous motor activity of mice as a reflection of the CNS depressant or sedative side effects of the test compound. It was carried out according to the method described in the foregoing Wu, et al. 1972 publication. Test III is similar except that the mice were treated orally. By reference to the data from Tests III and IV for Compound Nos. 2, 3, and 6, it is evident that the intraperitoneal route of administration reflects several-fold stronger activity than the oral route. The $AED_{-0.3}$ reflects approximately 50% reduction in spontaneous motor activity.

Test VII is an in vitro measurement of alpha-adrenergic receptor blocking action employing the isolated seminal vesicle of the rat. Alpha-adrenergic receptor blocking action is an undesired side effect of the major tranquilizers such as chlorpromazine. The strong alpha-adrenergic blocking activity thereof is reflected by the data in the table. The method of Test VII is that described in the foregoing Wu, et al. 1972 publication. The $IC_{50}$ value is the concentration of the test compound in solution which inhibits by 50% the contractile response of the tissue strip to 1-norepinephrine. A low value represents high activity.

Tests V and VI are receptor binding assays which measure the ability of a compound to prevent the binding of a radiolabeled ligand to specific high affinity sites in brain tissue. According to the state of the art, various ligands have been identified with aspects of CNS function or potential for side effects. The ability of a compound to inhibit labeled ligand binding in vitro is considered to be a reflection of the compound's ability to effect the corresponding CNS function or side effect in vivo.

Test V is a dopamine binding assay which reflects neuroleptic activity (Burt, Creese, and Snyder, Molec. Pharmacol. 12:800 (1976); Burt, Creese, and Snyder, Science 196: 326 (1977); Creese, Burt, and Snyder, Science 192: 481 (1976)). The corpus striatum of male Sprague-Dawley rats (Charles River Laboratories) is employed as the test tissue. The radiolabeled ligand is tritiated spiperone. In Test V any compound more active than clozapine ($IC_{50}=1000$ nM) is considered to have potential utility. Thus, any value less than 1000 nM in Test V represents potential neuroleptic utility.

Test VI employs tritiated (2,6-dimethoxyphenoxyethyl)aminomethyl-1,4-benzodioxane, also known as WB-4101, as radiolabeled ligand and receptor tissue of the cerebral cortex (Sprague-Dawley rats). WB-4101 is an alpha-adrenergic blocking agent and has a high affinity for alpha-adrenergic receptors in the cerebral cortex (Crews, et al., Science 202: 322 (1978); Rosenblatt, et al., Brain Res. 160: 186 (1979); U'Prichard, et al., Science 199: 197 (1978); U'Prichard, et al, Molec. Pharmacol. 13: 454 (1977)). In this test compounds having less than 1/10th the potency of phentolamine, which exerts $IC_{50}$ of 10 nM, are considered to be inactive. Thus, any compound having a value in excess of 100 nM is considered inactive.

Compound No. 4 is the preferred compound of the present invention. The substance has good potency in Tests I and V reflecting neuroleptic action, and low potency in Tests III and VI reflecting lack of sedative action and lack of alpha-adrenergic blocking action. It is distinguished from the prior art, and particularly Compound No. 3 the most structurally similar compound, with regard to neuroleptic potency in Test V, lack of sedative action which is high for Compound No. 3 (Tests III and IV). A low propensity for those undesired actions of Compound No. 4 is evident by comparing its values in Tests III and VI to Compound No. 6 which is known to have low activities of those types.

The other prior art pyridines, Compound Nos. 1 and 2, are very substantially less active in the conditioned avoidance response test reflected by the data for Test II. Compound No. 2 is in addition a relatively strong alpha-adrenergic blocking agent (Tests VI and VII).

Compound Nos. 4, 6, and 7 are each inactive at oral doses of 200 mg/kg. in the rat catalepsy test (Costall, B. and Naylor, R. J., Psychopharmacologia, 34, 233–241 (1974)) signifying low potential for provoking extrapyramidal symptoms (EPS). That dose of Compound No. 7, however, constituted the $ALD_{50}$ dose for rats. In mice the $ALD_{50}$ of Compound No. 7 was determined to be 500 mg/kg. of body weight. Chlorpromazine exhibits $ED_5 = 4.1$ mg/kg. in the rat catalepsy test in correlation with its known propensity for EPS.

The compounds of the present invention may be administered to mammals to exert their tranquilizer or neuroleptic and anxiolytic effects in the same way and in similar dosage amounts as are suitable for buspirone, and the other pyrimidines and pyridines claimed in the cited Wu, et al. patents. Information with respect to dosage, pharmaceutical formulations and administration is presented in the above cited U.S. Pat. Nos. 3,976,776 and 4,182,763. Likewise, the synthetic methods of U.S. Pat. No. 3,907,801 for the synthesis of the prior art pyridine Compounds 1, 2, and 3 are applicable to the synthesis of the compounds of the present invention and reference should be made to U.S. Pat. No. 3,907,801 for general information in this regard.

DESCRIPTION OF SPECIFIC EMBODIMENTS

In the following procedures temperatures are expressed in degrees centigrade (°). Melting points are uncorrected. The nuclear magnetic resonance (NMR) spectral characteristics for both the hydrogen nuclei (H NMR) and the 13 molecular weight carbon isotope nuclei ($^{13}C$ NMR) refer to chemical shifts ($\delta$) expressed as parts per million (ppm) versus tetramethylsilane (TMS) as reference standard. The relative area reported for the various shifts in the H NMR spectral data corresponds to the number of hydrogen atoms of a particular functional type in the molecule. The nature of the shifts as to multiplicity is reported as broad singlet (bs), singlet (s), multiplet (m), doublet (d), triplet (t), or doublet of doublets (dd) with coupling constants (J) reported where appropriate in both the H NMR and the $^{13}C$ NMR spectral data. The format is H NMR (solvent): $\delta$ (relative area, multiplicity, J value), and $^{13}C$ NMR (solvent): $\delta$ multiplicity. Abbreviations employed are DMSO-$d_6$ (deuterodimethylsulfoxide), CDCl$_3$ (deuterochloroform), and are otherwise conventional. The infrared (IR) spectral descriptions include only absorption wave numbers (cm$^{-1}$) having functional group identification value. The IR determinations were employed either using potassium bromide (KBr) as diluent, or with liquids using the film technique (film). The elemental analyses are reported as percent by weight.

PROCEDURE 1

8-[4-(1-Piperazinyl)butyl]-8-azaspiro[4.5]decane-7,9-dione

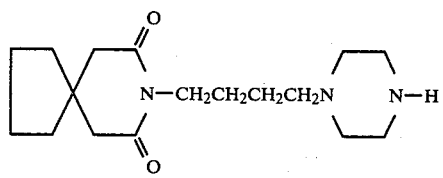

The following materials are charged to a 1 liter reaction flask containing 500 ml. of toluene, and the mixture is refluxed for 18 hours.

| | |
|---|---|
| 3,3-tetramethyleneglutaramide | 33.4 g., 0.2 moles |
| 1,4-dibromobutane | 43.2 g., 0.2 moles |
| Potassium carbonate | 103.7 g., 0.75 moles |

After the reflux period was completed, 64.6 g. (0.75 mole) of piperazine was added and heating at reflux was continued for an additional 7 hrs. The mixture was then filtered hot to remove insoluble material, and the filtrate was allowed to stand at room temperature overnight. Unreacted piperazine separated as a crystalline solid which was removed by filtration. The solvent was removed from the filtrate by vacuum distillation, and the residue was distilled at 180°–210°/0.1 mmHg, yield 23.56 g. (38%). Examination of the NMR spectrum indicated contamination of the product with a small amount of piperazine.

PROCEDURE 2

2-[4-[4-(7,9-Dioxo-8-azaspiro[4.5]decan-8-yl)butyl]-1-piperazinyl]pyridine-3-carbonitrile

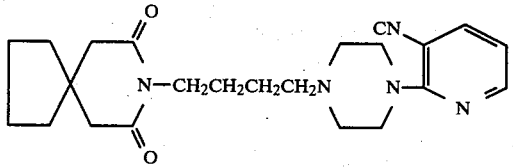

The product of Procedure 1, 5.0 g. (0.0163 mole) and 2.26 g. (0.0163 mole) of 2-chloro-3-cyanopyridine, 1.65 g. (0.0163 mole) triethylamine, and 40 ml. of ethanol were placed in a pressure vessel and the void space flushed with nitrogen before sealing. The vessel was then heated at 150° C. for 5 hrs. and allowed to cool overnight. The contents were removed and partitioned between 50 ml. of chloroform and 50 ml. of water. The chloroform layer was separated, dried, and the solvent removed by distillation yielding 6.27 g. of an oil. A portion of the latter weighing 5.68 g. was dissolved in chloroform and absorbed on a column containing 240 g. of silica. The column was developed first with 2.1 of chloroform which resulted in the removal of essentially none of the desired material and then with 2.5 l. of chloroform containing 2% by volume of ethanol. The first half of the CHCl$_3$/EtOH eluate yielded 3.4 g. of an oil the NMR spectrum of which corresponded to the desired product. The oil, 3.14 g., was dissolved in 25 ml. of ethanol, the solution chilled in an ice bath, and 2.56 ml. of 2.99 N ethanolic hydrochloric acid was added. The amount of hydrochloric acid employed was the stoichiometric amount required for formation of the monohydrochloride salt of the desired product. The salt failed to precipitate and the solution was concentrated to dryness and the residue triturated with ether resulting in partial crystallization thereof. The solid was dissolved in 250 ml. of acetone, filtered, and the solution poured into 300 ml. of ether resulting in precipitation of the desired monohydrochloride salt. It was dried in vacuo at the reflux temperature of toluene; yield 2.31 g., m.p. 180°–182°.

Anal. Found: C, 62.04; H, 7.29; N, 15.58. IR (KBr): 1130, 1240, 1360, 1440, 1580, 1670, 1720, 2220, 2450, and 2950 cm$^{-1}$.

H NMR (DMSO-d$_6$): 1.54 (12, m); 2.65 (4, s); 3.12 (4, m); 3.66 (6, m); 4.27 (2, m); 7.04 (1, dd, 7,8 Hz, 4.8 Hz); 8.14 (1, dd, 7.8 Hz, 2.9 Hz); 8.46 (1, dd, 4.8 Hz, 2.0 Hz).

$^{13}$C NMR (DMSO-d$_6$): 20.41, 23.66, 24.76, 36.82, 37.80, 39.08, 43.82, 44.71, 50.24, 55.00, 95.75, 115.99, 117.26, 144.19, 151.96, 159.76, 172.09.

PROCEDURE 3

8-[4-(2-Methyl-4-[phenylmethyl]-1-piperazinyl)-butyl]-8-azaspiro[4.5]decane-7,9-dione

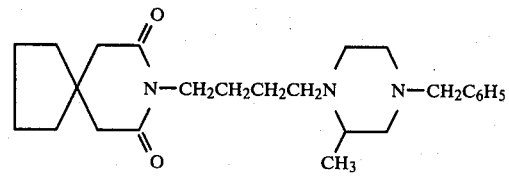

2-Methyl-4-benzylpiperazine dimaleate was prepared according to the method of Cignarella, et al., Il. Farmaco. Ed. Sc., Volume 34, page 820, This material, 16.9 g. (0.04 mole), was refluxed in 400 ml. of acetonitrile as reaction medium with 12.1 g. (0.04 mole) of 8-(1-bromo-4-butyl)-8-azaspiro[4.5]decane-7,9-dione, 16.6 g. (0.12 mole) of potassium carbonate, and a few crystals of potassium iodide for 20 hrs. The solvent was removed by distillation in vacuo, the residue dissolved in 150 ml. of ether, insoluble material removed by filtration, and the ether removed by distillation in vacuo. The residue was an oil weighing 17.2 g. which was dissolved in 100 ml. of ethanol, acidified with 11.06 ml. of 7.6 N hydrochloric acid and set aside to cool. The desired material crystallized as the dihydrochloride salt ¼ molecular proportion hydrate and was recovered by filtration; yield 15.58 g., (80%), m.p. 238°–240°.

Anal. Found: C, 61.45; H, 7.97; N, 8.35; H$_2$O 0.57.

IR: 1130, 1360, 1450, 1670, 1720, 2450, and 2950 cm$^{-1}$.

H NMR (DMSO-d$_6$): 1.36 (3, d, 6.0 Hz); 1.50 (12, m); 2.60 (4, s); 3.50 (11, m); 4.33 (2, s); 3.90 (2, bs).

The starting material 8-(1-bromo-4-butyl)-8-azaspiro[4.5]-decane-7,9-dione was prepared as described in Procedure 1 prior to addition of the piperazine reactant except that the amount of 1,4-dibromobutane employed was doubled. The product was isolated after removing insoluble material by filtration of the hot reaction mixture, evaporating the toluene from the filtrate, and distilling the residue in vacuo, b.p. 160°–167°/0.1 mmHg, yield 35.2 g. (58%).

PROCEDURE 4

4-(2-Methyl-1-piperazinyl)butyl]-8-azaspiro[4.5]decane-7,9-dione

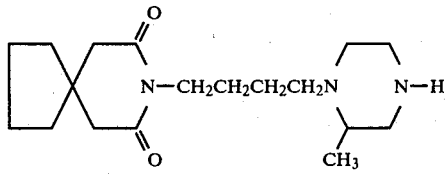

The product of Procedure 3, 15.58 g. (0.031 mole) is suspended in 110 ml. of water and hydrogenated over 2 g. of a 10% palladium-on-carbon catalyst at 67 g and room temperature. After hydrogen absorption had ceased, the catalyst was removed by filtration and water was removed from the filtrate by vacuum distillation. The residue was crystallized from 40 ml. of ethanol and the product dried to constant weight; yield 4.49 g. of the dihydrochloride salt, m.p. 215°–217°.
Anal. Found: C, 54.48; H, 8.21; N, 10.64.
IR (KBr): 1125, 1360, 1370, 1400, 1670, 1722, 2660, and 2950 cm$^{-1}$.
H NMR (DMSO-d$_6$): 1.39 (3, d, 6.0 Hz); 1.50 (12, m); 2.61 (4, s); 3.40 (11, m); 10.10 (3, bs).
$^{13}$C NMR (DMSO-d$_6$): 13.50 q, 19.95 t, 23.61 t, 24.65 t, 36.77, 37.60, 39.05, 43.79 t, 44.50, 50.61 t, 54.00 d, 55.34 s.

PROCEDURE 5

[4-[4-(7,9-Dioxo-8-azaspiro[4.5]decan-8-yl)butyl]-3-methyl-1-piperazinyl]pyridine-3-carbonitrile

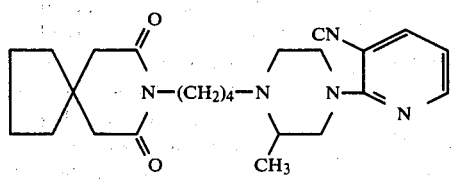

The product of Procedure 4, 3.38 g. (0.0105 mole) is caused to react with 1.46 g. (0.0105 mole) of 2-chloro-3-cyanopyridine in the presence of 1.06 g. (0.0105 mole) of triethylamine in 40 ml. of ethanol in a pressure vessel as described in Procedure 2. The crude product, 3.58 g., was recovered as an oil which was dissolved in 30 ml. of ethanol and treated with 2 molecular proportions of ethanolic hydrogen chloride. The solvent was removed by distillation, and the residue was dried by azeotropic distillation with benzene which resulted in crystallization of the desired product as the monohydrochloride, m.p. 181°–183°.
Anal. Found: C, 62.45; H, 7.48; N, 15.16.
IR (KBr): 1135, 1350, 1440, 1580, 1670, 1720, 2220, 2660, and 2950 cm$^{-1}$.
H NMR (DMSO-d$_6$): 1.50 (15 m); 2.62 (4, s); 3.50 (9, 1); 4.16 (2, m); 7.02 (1, dd, 7.8 Hz, 4.9 Hz); 8.14 (1, dd, 3 Hz, 1.9 Hz); 8.45 (1, dd, 4.9 Hz, 1.9 Hz); 11.70 (1, bs).

PROCEDURE 6

8-[4-(3-Methyl-1-piperazinyl)butyl]-8-azaspiro[4.5]decane-7,9-dione

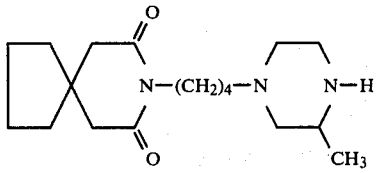

A mixture of 8-(1-bromo-4-butyl)-8-azaspiro[4.5]decane-7,9-dione prepared as described in Procedure 3, 8.14 g. (0.027 moles), and 5.41 g. (0.054 moles) of 2-methylpiperazine was heated at reflux in 40 ml. of toluene overnight. The by-product 2-methylpiperazine hydrobromide was removed by filtration and the solvent was distilled from the filtrate in vacuo. The residue was dissolved in chloroform and extracted with 100 ml. of 1.5 N aqueous hydrochloric acid. The product was recovered from the aqueous extract by neutralization with sodium hydroxide and extraction into chloroform. After drying and evaporation of the chloroform, the crude product was obtained as a residue weighing 9.76 g. It was distilled in vacuo, b.p. 180°–185° C./0.01 mmHg; yield, 6.22 g. A portion of this material weighing 1.5 g. was dissolved in 10 ml. of ethanol and converted to the hydrochloride salt by treatment with sufficient ethanolic hydrogen chloride to provide the dihydrochloride salt. The solvent was distilled in vacuo, and the residue was crystallized from a mixture of 10 ml. of ethanol and 35 ml. of acetone yielding the monohydrochloride which crystallized as the hemihydrate; yield, 1.05 g., m.p. 196°–198° C.
Anal. Found: C, 53.61; H, 8.37; N, 10.06; H$_2$O, 2.57.
IR (KBr): 1125, 1215, 1360, 1440, 1670, 1725, 2700, and 2950 cm$^{-1}$.
H NMR (DMSO-d$_6$): 1.51 (15, m); 2.80 (4, s); 3.85 (11, m); 10.60 (3, bs).
$^{13}$C NMR (DMSO-d$_6$): 15.14 q, 20.41 t, 23.61 t, 24.56 t, 36.78 t, 37.73, 39.04, 39.30, 43.78 t, 46.90 d, 47.90 t, 52.15 t, 55.10 t, 172.10 s.

PROCEDURE 7

2-[4-[4-(7,9-Dioxo-8-azaspiro[4.5]decan-8-yl)-butyl]-2-methyl-1-piperazinyl]pyridine-3-carbonitrile

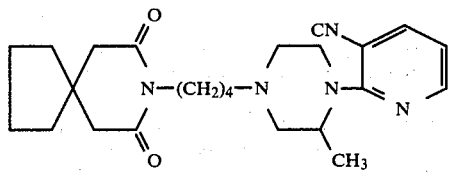

The product of Procedure 6 is allowed to react with 2-chloro-3-cyanopyridine as described in Procedures 2 and 5 to yield this substance.

PROCEDURE 8

2-Chloro-3-methoxypyridine 3-methoxy-2-(1H)pyridone, 10 g. (0.08 mole), 12.3 g. (0.08 mole) of phosphorus oxychloride, and 11.9 g. (0.08 mole) of N,N-diethylaniline are combined in a suitable reaction vessel and heated at reflux for 20 hrs. The reaction mixture was allowed to cool, and was then mixed with 200 ml. of water and ice. The aqueous mixture was extracted with ether and the extracts dried over magnesium sulfate. The drying agent was then removed by filtration and the solvent was removed from the filtrate by distillation in vacuo. The residue was extracted with 160 ml. of boiling hexane and the hexane extracts decanted from the residue while still hot. The hexane solution was cooled in ice resulting in precipitation of the desired produce, weight 7.5 g., m.p. 46°–48°.

PROCEDURE 9

4-(3-Methoxy-2-pyridinyl)piperazine

2-Chloro-3-methoxypyridine, 7 g., 0.05 mole) was allowed to react with 21.5 g. (0.25 moles) of piperazine in the presence of 34.5 g. (0.25 mole) of pulverized potassium carbonate employing 150 ml. of amyl alcohol as reaction medium. The mixture was heated at reflux in a round bottom flask after drying the reaction mixture by distillation. A reflux period of 20 hrs. following elimination of the water was employed. The reaction mixture was filtered while hot and the solvent was removed from the filtrate by distillation. The residue was triturated with chloroform and 1 g. of solid was removed by filtration. The chloroform was removed from the filtrate by distillation yielding 3.88 g. of the desired product which was purified by distillation, b.p. 120°–124°/0.1 mmHg.

Anal. C, 61.72; H, 8.03; N, 20.83.

IR (film): 790, 1020, 1110, 1210, 1240, 1450, 1470, 1590, 2835, and 2940 cm$^{-1}$.

H NMR (CDCl$_3$): 1.91 (1, s); 3.05 (4, m); 3.36 (4, m); 3.84 (3, s); 6.77 (1, dd, 5.0 Hz, 7.8 Hz); 7.00 (1, dd, 1.9 Hz, 7.8 Hz); 7.85 (1, dd, 1.9 Hz, 5.0 Hz).

PROCEDURE 10

8-]4-[4-(3-Methoxy-2-pyridinyl)-1-piperazinyl]-butyl]-8-azaspiro[4.5]decane-7,9-dione 4-(3-Methoxy-2-pyridinyl)piperazine, 4.87 g. (0.025 mole), was allowed to react with 7.62 g. (0.025 mole) of 8-(1-bromo-4-butyl)-8-azaspiro[4.5]decane-7,9-dione prepared as described in Procedure 3 in the presence of 2.53 g. (0.025 moles) of triethylamine employing 60 ml. of ethanol as reaction medium. The reaction was carried out in a pressure vessel at a temperature of 150° C. for 6½ hours in the same fashion as described in Procedure 2. After allowing the reaction vessel to cool to room temperature, it was opened and the reaction mixture was concentrated by distillation of the solvent in vacuo. The residue was dissolved in chloroform and washed with 30 ml. of aqueous 1 N sodium hydroxide, and then with 40 ml. of water. The chloroform solution was dried over magnesium sulfate and the chloroform removed by distillation in vacuo, yielding 10.49 g. of the desired product. This material was purified by column chromatography employing a column containing 250 g of silica developed with chloroform containing 5% by volume of ethanol. The product was isolated from the eluate and weighed 5.96 g. This crude material was converted to the dihydrochloride salt by dissolving in 50 ml. of ethanol and treating the solution with hydrogen chloride. Insoluble material was removed by filtration and the filtrate was treated with 200 ml. of ether which resulted in precipitation of the dihydrochloride salt of the desired product, m.p. 194°–196°, yield 5.56 g Anal. C, 57.02; H, 7.62; N, 11.46.

IR (KBr): 790, 1000, 1130, 1240, 1345, 1440, 1600 1665, 1725, 2560, 2860, and 2950 cm$^{-1}$.

H-NMR (DMSO-d$_6$): 1.55 (12, m); 2.65 (4, s); 3.12 (4, m); 3.64 (6, m); 3.91 (3, s); 4.24 (2, m); 7.12 (1, dd, 5.3 Hz, 8.0 Hz); 7.62 (1, m); 7.78 (1, m); 11.40 (1, bs); 11.90 (1, bs).

What is claimed is:

1. A compound selected from the group consisting of those having the formula and the pharmaceutically acceptable acid addition salts thereof wherein R$^1$ and R$^2$ are selected from the group consisting of hydrogen and methyl, and R$^3$ is cyano.

2. The compound of claim 1, 2-[4-[4-(7,9-dioxo-8-azaspiro[4.5]decan-8-yl)butyl]-1-piperazinyl]pyridine-3-carbonitrile or a pharmaceutically acceptable acid addition salt thereof.

3. The compound of claim 1, 2-[4-[4-(7,9-dioxo-8-azaspiro[4.5]decan-8-yl)butyl]-3-methyl-1-piperazinyl]-pyridine-3-carbonitrile or a pharmaceutically acceptable acid addition salt thereof.

4. The process for eliciting a tranquilizer effect in a psychotic mammal which comprises administering to said mammal a non-toxic neuroleptically effective dose of from 0.01 to 40 mg/kg. of body weight of said mammal of a compound claimed in claim 1 by the oral or a parenteral route.

5. A method for the palliative treatment of neurosis in which anxiety symptoms are prominent which comprises administering a non-toxic anxiolytically effective dose of a compound claimed in claim 1 to a neurotic patient by the oral or a parenteral route.

6. A pharmaceutical composition in dosage unit form suitable for systemic administration to a mammalian host comprising a pharmaceutical carrier and an amount of a compound claimed in claim 1 to provide an effective daily dose of from 0.01 to 40 mg/kg. of body weight of said host.

7. The compound of claim 1, 2-[4-[4-(7,9-dioxo-8-azaspiro[4.5]decan-8-yl)butyl]-2-methyl-1-piperazinyl]pyridine-3-carbonitrile or a pharmaceutically acceptable acid addition salt thereof.

* * * * *